United States Patent [19]

Setala

[11] 4,022,883

[45] May 10, 1977

[54] COMPOSITION FOR ALLEVIATION OF UREMIC SYMPTOMS AND METHOD FOR ITS PREPARATION

[75] Inventor: Kai Martin Setala, Helsinki, Finland

[73] Assignee: Bioscal GmbH, Flensburg, Germany

[22] Filed: Mar. 18, 1975

[21] Appl. No.: 559,525

[30] Foreign Application Priority Data

Mar. 23, 1974 Germany .......................... 2414156

[52] U.S. Cl. .................................. 424/93; 424/94
[51] Int. Cl.$^2$ ....................................... A61K 37/00
[58] Field of Search ............................... 424/93, 94

[56] References Cited

UNITED STATES PATENTS

| | | | |
|---|---|---|---|
| 3,701,830 | 10/1972 | Weinrich et al. | 424/94 |
| 3,865,726 | 2/1975 | Chibata et al. | 424/94 X |

Primary Examiner—Frederick E. Waddell
Attorney, Agent, or Firm—Toren, McGeady and Stanger

[57] ABSTRACT

The invention concerns an orally administered composition, i.e. a medically active agent for alleviation of uremic symptoms and a method for its preparation. The invention is based on the surprising observation that non-protein nitrogen compounds which accumulate in the body of uremic patients herein referred to as (NPN compounds: in the literature often designated as "uremia toxines") may be biodegraded and biosynthetized to harmless metabolites by utilizing selected non-pathogenic soil microorganisms, as a result of the action of these microorganisms in the intestine of the patient. In this way, at least part of the NPN compounds may be non-toxified, i.e., utilized by the organism. It is also observed that the NPN compounds, as such, do not represent any worthless "waste products" which necessarily have to be excreted. Instead only an excess of NPN not required and not utilized is excreted under normal circumstances. Further, the NPN:s do not constitute "end products" but are potentially valuable intermediates which allow a so called shuttle traffic in the internal metabolism, in other words: synthesis ⇌ degradation ⇌ resynthesis. In order to prevent an excess enrichment of unwanted NPN compounds in the body of patients suffering from irreversible progressive renal failure, the processes responsible for the internal metabolism must be "cycled backwards".

6 Claims, No Drawings

COMPOSITION FOR ALLEVIATION OF UREMIC SYMPTOMS AND METHOD FOR ITS PREPARATION

BACKGROUND OF THE INVENTION

The object of the invention is to provide a composition for alleviation of uremic symptoms, which principle has a specific NPN compounds degrading effect, by utilizing non-pathogenic soil bacteria introduced into the intestine of persons suffering from uremia, whereby a biodegradation of NPN compounds possibly followed by a biosynthesis is made possible. Furthermore, the formation and concentration of nitrogen containing waste products in the organism is reduced.

To demonstrate the frequency of renal diseases, the following may be cited: in the forewords of The Manual of Artificial Organs, Vol. 1: The Artificial Kidney (author Y, Nose, Mosby Co., Saint Louis 1969) W. J. Kolff writes e.g. "the more we are worried and unhappy over the fact that only 1.5% of the 40,000 persons in need are helped by kidney transplantation or the artificial kidney, the more we search for a solution to the cruel problem caused by chronic renal failure". W. J. Kolff writes further in the forewords of "Hämodialyse und Peritonealdialyse" (authors P. Dittrich et al., Springer Verlag, Berlin Heidelberg New York 1969) that two high level committees, the Gotschalk-committee and the Burton-committee, have presented remarkably objective reports in the United States. If all those 40,000 patients which need dialysis or kidney transplantation were to be treated, the costs in the United States would be 600,000,000 dollars per year. But as stated earlier only one and a half percent are treated and rest are simply left to die. It is to be remembered that the number of lethal automobile accidents in the United States was 57,000 in the year 1966. This number is comparable with the number of uremia patients per year who are in a final stage of the illness and who would be considered for kidney transplantation.

Regarding uremic syndrome the following manuals are referred to: "Hämodialyse and Peritonealdialyse", P. Dittrich et al., Springer Verlag, Berlin Heidelberg New York, 1969; "The Kidney", A. Golden and J. F. Maher, Williams and Wilkins Co., Baltimore, 1971; "Uremia: Progress in Pathophysiology and Treatment", J. P. Merrill and C. L. Hampers, Grune and Stratton, New York, 1971.

The following terms are used interchangeably herein: Uremic syndrom = chronic progressive irreversible renal failure = irreversible functional disorder of the kidneys.

Basic pathogenesis: for the time being unknown, only the symtoms are known. It is a complex symptom which often relates to increased metabolite retention values in the body fluids. There is often little conformity between chemical determinations and clinical observations. It is not known which of the numerous NPN compounds measured in the blood and other body fluids are toxic and/or responsible for the uremic symptoms. Guanidine is one of the NPN:s which has been considered "toxic". The blood-fluid limit might change into uremia. Urea possibly influences the migration of other NPN compounds through the physiological membranes and possibly plays an important role in the diffusion of more toxic substances into the urine.

Severe uremia brings forth general incapability. The patients are weak in conjunction with having other symptoms, as for example sickness, anorexia, vomiting, loss of weight, incapability of mental concentration, hypertony including its different consequences which often follow from renal failure and add to the symptoms. In many patients, different degrees and types of anemia and/or protein and/or salt exhaustion might influence the cell nutrition. All changes cannot be related to the retention of urea and other NPN compounds in the organism. Water intoxication, non-equilibrium in the K- and Na-distribution could be important. In addition, neuronal changes appear. Depression of the central nervous system and neuromuscular irritability have been declared as effects of, e.g., guanidine. The heart and pericardial structures might be influenced. The lungs might show signs of uremic pneumonitis. Pathological changes in the gastrointestinal tract are frequent. Certain serum enzymes might undergo changes in uremic patients. Anemia develops because of bone marrow suppression and/or hemolysis.

In the present therapy of uremia, it is noted that it includes kidney transplantation and dialysis, such as, hemodialysis, peritoneal dialysis and different enterodialysises or gastrointestinal drainage, respectively, with or without diet of energy rich, high quality nutrition. Kidney transplantation can for different reasons be carried out on only a limited number of kidney patients. There is for example a shortage of suitable donors. Basic immunologic principles are still unsolved. In some cases the transplanted kidney will be affected in the same way as the original one.

The method mostly used in connection with cronic renal insufficiency is the hemodialysis. The blood of the kidney patient is dialyzed, e.g. once a week or every second or every third day, year in, year out. Large amounts of accumulated NPN compounds (uremic "waste substances") are removed from the blood by hemiodialysis. Thereby the blood-urea concentration for example during a hemodialysis lasting about 8 hours, decreases about 50% compared to the initial value. But the NPN values in the blood increase rapidly again, e.g., the serum-creatine value reaches its initial value within about 24 hours. Peritoneal dialysis is principally almost as effective as hemodialysis; it must also be carried out repeatedly. Its usefulness is limited and it cannot be used continuously.

Certain amounts of urea may be removed also by enterodialysis or gastrointestinal drainage. These methods cannot be repeated several times. Furthermore, NPN compounds, such as, e.g. creatinine, are not removed from the blood.

It may be concluded that the human body seems to be lavish in its excretion of NPN compounds through the kidneys. Actually huge amounts leave the organism, as, for example, urea 25 to 35 g daily (= 8 to 12 kg yearly), uric acid 0.6 to 0.9 g daily (= 0.2 to 0.3 kg yearly) and creatinine 1 to 2 g daily (= 0.3 to 0.7 kg yearly).

In ruminant egg, proteins are synthesized directly from hydrolyzed urea by microorganisms. A diet containing small amounts of nitrogen and large amounts of carbohydrates favours the protein synthesis. The re-use of "waste nitrogen" presumably lessens the animal's dependence on environmental protein sources. Sheep on a low protein diet are able to re-use at least 50% of the daily produced endogenous urea instead of excreting it. Experiments on ruminants show furthermore that creatinine is metabolized by rumen bacteria with the production of ammonia: creatine and creatinine is degraded by rumen microorganisms to urea and sarcosine. Part of the ammonia ($NH_3$) formed in the rumen is used by the bacteria for synthesis of cell constituents. Part is absorbed through the ruminal wall into the portal blood stream. Part leaves the rumen into the lower portions of the intestine. The capability of the ruminal bacteria to use ammonia is dependent on the simultaneous availability of other nutrients requried for the synthesis of their cellular constituents. Especially important are suitable carbon and energy sources. The presence of inorganic ions for the rumen-urease activity is critical. The results show that the urease activity is stimulated by the presence of Mn, Mg, Ca, Sr and Ba. Mn is the most effective. The ruminal bacteria produce and require B vitamins. The branched volatile fatty acids apparently play an important role in providing a carbon skeleton for the biosynthesis of those amino acids which are not synthesized by certain rumen bacteria. Besides the degradation of urea, different microorganisms, because of the enzyme system contained therein, are capable of degrading creatine, creatinine, uric acid and so on, that is, those NPN compunds which accumulate in the organism of uremic patients. The formation of some of the enzyme systems in the organism depends on the presence of the substrate in the medium. The enzymes responsible for the oxidation of creatinine, lactose or malonic acid, are "totally adaptive", i.e. they are not formed in the absence of the substrate in question. The enzymes responsible for the degradation of several other substances, as for example uric acid, amino acids, lactic acid are "partly adaptive", i.e. their formation occurs to a certain degree in the absence of the substrate from the medium and is highly increased by its addition to the medium. Other enzyme systems, as, for example, those responsible for the oxidation of glucose or glycerol are constitutive.

In humans, the following aspect on the NPN metabolism may be considered. Urea hydrolysis takes place in the gastrointestinal tract and depends exclusively on bacteria. The digestion in ruminants stays in a definite close connection with that in monogastric animals. In adults, the gastrointestinal tract/the intestine is inhabited by several species, types and strains of microorganisms. The amount of microorganisms in the human (large) intestine is enormous: thus one milligram of feces contains about 150,000,000 microorganisms, and bacteria form about ⅔ of the dry feces. A few days after birth the intestine flora starts to develop and the blood-coagulation time becomes normal as a result of the bacterial synthesis of vitamin K in the intestine. In adults, intestinal bacteria synthesize numerous vital substances. In patients suffering from chronic progressive irreversible renal failure, e.g., enterodialysis results in a passive crossing of the mucous membranes following differences between gradients, e.g. urea, and others pass by means of active forces (part of the electrolytes). From the point of view of the invention, it is important that the movement of urea takes place rapidly.

Concerning uremic patients, the utilization of urea-nitrogen for the protein synthesis has been discussed. The consequences of irreversible renal failure are, as known, directly related to the amount/degree of protein catabolism. When this can be minimized not only is the accumulation and retention, respectively, of NPN compounds delayed and decreased, but also, the load of K, P and so on, and their disappearance are prevented. One of the goals in the treatment of irreversible renal failure is to keep the nitrogen balance on the lowest possible intake of low-value proteins and/or amino acids. Some results have been obtained in the treatment of uremic patients on a corresponding diet, presumably because the nitrogen balance is kept in equilibrium by the intake of essential amino acids and high-value proteins. Investigations of the urea metabolism during low protein intake have shown that e.g. nitrogen from urea, apparently via bacterial hydrolysis to ammonia, may be used for protein synthesis. Urea production is reduced on a low protein diet but the urea degradation is sustained. It has further been shown that if the nutritional problem is tackled by means of a suitable diet in the case of renal failure, it is likely that at least some of the clinical problems, such as, acidosis, hyperkalemia, and phosphate retention will disappear, as well as some of the symptoms of uremia which probably are caused by urea itself. Urea has been administered to children during the investigation of certain problems in order to show that children are able to utilize urea and some other simpler nitrogen containing substances. It has also been suggested to "cycle backwards" the urea metabolism in the organism under favourable circumstances. It has further been suggested that the urea production in patients with renal failure is dependent on the protein intake down to a value of 20 g/day. A low protein diet consisting of so called natural foods suitable for uremic patients usually contains too few calories, i.e., energy. On the other hand, the addition of a purely of carbohydrate containing caloric supplement reduces urea production to a significant degree. In most kidney patients treated in this way, 20 to 80 percent of the urea formed is metabolized extrarenally. A literature study relating to the production and extra-renal (outside the kidneys) metabolism of urea in kidney patients treated with diet and dialysis, show that a substantial extra-renal urea degradation can occur in these patients, and further, that a reduction of the urea pool in the organism by dialysis, reduces urea degradation and furthermore that increased urea degradation in the presence of high body fluid urea concentration may be an effect of adaptive enzymes or represent reversal of the urea cycle.

In the human environment, there are microorganisms, or soil bacteria which are able to biodegrade or decompose, respectively, those NPN compounds which also accumulate in the body of kidney patients. Experiments with some of the soil bacteria have shown that the bacterial enzymes are easily adaptable. Furthermore, the optimal pH value and growth temperature required for maximum biodegradation of e.g., creatinine are similar to the values inside the rumen. The enzyme systems of the soil bacteria are relatively specific for known creatinine and creatine. Thus, for example, creatine biodegrading soil bacteria, during the degradation, refuse compounds closely related to creatinine, or affect them only slowly. It should also be noted that most of the soil bacteria are usually non-pathogenic for humans when administered per os, i.e., when introduced via the digestive canal into the organism.

The microbial flora in the human digestion system may be influenced in many different ways. Even implantation, enrichment or replacement of a number of microorganisms in the gastrointestinal tract is possible. Purposeful administration of "trained" and "untrained", respectively, microorganisms has already been carried out as a therapeutical method. The administered microorganisms do however in the therapeutical treatment relatively rapidly disappear from the gastrointestinal tract after interruption of the treatment. On the other hand, microorganisms might live longer in the gastrointestinal tract provided that specific substrates together with other vital building components are present.

It has now surprisingly been found that uremic symptoms may be removed in patients by administering per os, a medical preparation that comprises — and this is the invention — a basic component of a system derived from non-pathogenic soil bacteria having the characteristics of degrading non-protein nitrogen compounds (NPN) and being active in the gastrointestinal tract. The basic component prepared by utilizing soil bacteria contains specific, constitutive enzyme systems having the characteristics of degrading NPN compounds.

The soil bacteria may also be administered in lyophilized form.

The composition contains as urea degrading soil microorganisms, Serratia, species and as creatinine degrading soil bacteria, a. non-fluorescent Pseudomonas or
b. Rhizobium or
c. Agrobacterium or
d. *Corynebacterium ureafaciens* or
e. *Arthrobacter ureafaciens* or
f. *Escherichia coli* or
g. *Pseudomonas aeruginosa*;

and as uric acid biodegrading soil microorganisms a. non-fluorescent species of Pseudomonas or
b. *Bascillus subtilis* or
c. *Bacillus fastidosus* or
d. *Micrococcus dentrificans* or
e. *Mycobacterium phlei* or
f. *Aerobacter aerogenes* or
g. *Fusarium moniliforme* or
h. *Histoplasma capsulata* or
i. *Penicillinum chrysogenum*.

The invention concerns also a method for the production of a composition for alleviation of uremic symptoms comprising selecting the species of urea degrading microorganism and cultivating this to determine that only one cell type grows in the culture medium, having the following composition: thiamine, pyridoxine, Ca-pantothenic acid, nicotinic acid, p-amino benzoic acid, each in an amount of 0.25 mg, 0.05 mg of folic acid, 1 $\mu$g of $B_{12}$-vitamin, 0.5 of $\mu$g biotine, 1.0 g of $K_2HPO_4$, 1.5 g of $NaH_2PO_4 \cdot 4H_2O$, 0.05 g of $MnCl_2 \cdot 4H_2O$, 0.1 g of $MgSO_4 \cdot 7H_2O$, 0.01 g of $FeSO_4 \cdot 7H_2O$, 1.0 g of yeast extract and 10 g/1000 ml of urea, at a pH value of 7.0 to 7.5. If urea is used as a nitrogen source 5.0 g/1000 ml of glucose or glycerol is added, the bacteria culture is cultivated at 28° C in a fermentation vessel, the cell mass washed repeatedly with a buffer solution having a pH value of 7.2 and centrifugated, and thereafter added to 1 molar glucose solution at a ratio of 1:1 as stabilisator, whereafter the product is freezed in liquid nitrogen, thereafter lyophilized 48 to 72 hours at −50° C and 0.03 torr, while being protected from atmospheric oxygen, is exposed to an inert gas, such as argon, dried and the dried product formed into orally administrable preparations, such as, capsules or the like.

Numerous investigations both in vitro as well as in vivo, i.e., using a living object, have been carried out with the principle. The investigations in vivo comprised animal experiments (dogs) and clincal experiments (voluntary test persons as well as uremic patients). The effect and the method of preparation of the priciple according to the invention is illustrated in following test results and examples.

EXPERIMENT 1

Firstly, it is shown that components exist in the human gastrointestinal tract which are capable of biodegrading NPN compounds in vitro. The contents of the intestines of test persons divided into three groups was collected. Group I consisted of 5 uremic patients who no longer showed any renal activity and who regularly received hemodialysis. Group II consisted of 5 patients with renal failure of a lesser degree and who for the time being did not need any hemodialysis. Group III consisted of 5 adults with normal renal functions. An infinitesimal amount of faeces (point of a needle) was inoculated with either creatine, creatinine or uric acid as a substrate in autoclaved test tubes. Principally the culture media contained as little nutrients as possible. The quantitative biodegradation capacity of all three NPN compounds were measured separately by means of conventional spectrophotometric methods. The growth of the microorganisms was followed regularly by generally accepted and known bacteriological methods. The difference: amount of NPN substrate initially present minus left-over (=remaining) NPN substrate was measured quantitatively in each individual experimental series. When bacterial growth could be established the identification of the microorganisms was carried out in a known manner. Results: The intestinal bacteria of group I (uremics) were capable of biodegrading significant amounts of creatine, creatinine and uric acid. In groups I and II (kidney patients from both groups) there were many cases (patients) which utilized up to 100 percent of the NPN compound in question. The intestinal bacteria of group III (healthy test persons) were almost incapable of utilizing the three NPN compounds under identical-/analogical experimental circumstances. Conclusion: It could thus be established that the intestinal bacteria in kidney patients were capable of degrading in vitro creatine, creatinine and uric acid when only one of these NPN compounds served as the sole substrate, probably by means of adapted enzyme systems of the soil bacteria.

EXPERIMENT 2

Thereafter was shown that certain bacteria in the human gastrointestinal tract are capable of decomposing NPN compounds in vitro.

In a series of 15 test tubes for each group a sole NPN compound, e.g., creatine, creatinine, or uric acid was used as the sole substrate. The growth rate of the bacterial cultures and their capability of decomposing the NPN compound was determined as above in experiment 1, with the result that some species of Pseudomonas were found most active. They grew fast on these barren media and biodegraded large amounts of NPN compounds: active were also some strains of *Escherichia coli*, Enterococcus, Proteus, Klebsiella. Conclusion: Under controlled experimental circumstances, pure cultures of laboratory microorganisms were capable of biodegrading e.g. creatine, creatinine and uric acid when these NPN compounds each were used alone as the sole substrate. The bacteria were chosen among those which are known to live in the human intestine under physiological circumstances.

source. The bacterial liberation of ammonia ($NH_3$) was determined simultaneously. Table 1 shows the distribution of the 729 isolated soil bacteria strains in groups corresponding to their specific capability of using the 12 NPN compounds as a substrate.

Table 1

| NPN compound | NPN as the sole nitrogen source | | NPN as nitrogen and carbon source | | Simultaneous liberation of $NH_3$ when NPN is the sole nitrogen source | | | | Total number of strains tested |
|---|---|---|---|---|---|---|---|---|---|
| | | | | | $NH_3$ not liberated | | $NH_3$ liberated | | |
| | Number of strains | % | Number of strains | % | Number of strains | % | Number of strains | % | |
| Urea | 521 | 71.1 | Not tested | | 64 | 19.0 | 273 | 81.0 | 337 |
| Guanidine | 377 | 51.8 | Not tested | | 80 | 47.8 | 87 | 52.2 | 167 |
| Ornithine | 637 | 87.3 | 302 | 41.5 | 129 | 54.0 | 110 | 46.0 | 239 |
| Arginine | 570 | 78.3 | 489 | 67.0 | 88 | 29.8 | 207 | 70.2 | 295 |
| Creatinine | 432 | 59.3 | 170 | 23.4 | 96 | 58.1 | 69 | 41.9 | 165 |
| Creatine | 322 | 41.4 | 171 | 23.5 | 103 | 72.1 | 40 | 27.9 | 143 |
| Uric acid | 595 | 81.6 | 446 | 61.1 | 89 | 33.4 | 177 | 66.6 | 266 |
| Glutaminic acid | 590 | 81.0 | 431 | 59.1 | 81 | 28.0 | 206 | 72.0 | 287 |
| Histidine | 631 | 87.9 | 517 | 71.0 | 145 | 40.1 | 217 | 59.8 | 362 |
| Xanthine | 478 | 65.6 | 279 | 38.3 | 94 | 40.5 | 138 | 59.6 | 232 |
| Allantoin | 657 | 90.0 | 417 | 57.1 | 84 | 30.4 | 192 | 69.5 | 276 |
| Agmatine | 620 | 86.0 | 504 | 69.2 | 75 | 25.2 | 223 | 74.9 | 298 |

EXPERIMENT 3

A large amount of soil samples was collected in order to determine the NPN biodegradation capability of soil bacteria which subsequently were isolated by culturing. The samples originated from ploughland, pastures, different types of cultivated grounds, grounds surrounding slaughterhouses, and zoological gardens containing bird excrements. The samples were collected in the South of Finland (Helsinki) during the summer. Thus it was already known that the optimal growth of temperature of the soil microorganisms had to be lower than in the Mediterranean countries. The samples were cultivated, isolated and identified by conventional bacteriological methods. Also in this experiment, the biodegrading capacity of the isolated pure cultures of the soil bacteria was tested by using NPN compunds, using only one of the following components as the sole barren substrate: urea, guanidine, ornithine, arginine, creatine, creatinine, uric acid, glutaminic acid, histidine, anthine, allantoine and agmatine. These NPN compounds were selected because of their key position in the internal metabolism. Harvesting, basic cultivation and enrichment of the soil microorganisms were performed at 28° C.

Results: Altogether 729 strains of soil bacteria were isolated by cultivating in about 100,000 individual cultures. Each of the 12 NPN compounds was used alone in a series as the only nitrogen source and in a parallel series simultaneously both as the nitrogen and carbon source.

Special measurements were carried out on diagnostic media for visual examination of the extracellular and intracellular fermentation. All 12 NPN compounds were microbiologically decomposed. Of the 729 examined soil bacteria, there were about 30 which had the capacity to biodegrade all of the 12 NPN compunds, either simultaneously or after an adaptation interval. Table 1 shows further that 521 (71.1%) of the 729 soil bacteria strains could utilize urea as the sole nitrogen source. 7 strains (577-579, 588, 677 and 722) showed a remarkably high degradation capacity. It was further shown that if the urea degradation capacity of a given soil bacteria was especially high, the capacity to simultaneously biodegrade other NPN compounds was in most instances significantly lower. Table 2 shows the biodegradation of urea by some strains of soil bacteria, selected at random, after 30 minutes incubation at +37° C. The material also comprised strains of bacteria which were able to degrade even 85 mg (i.e 85%) of urea out of 100 mg under the same experimental circumstances.

Table 2

| No. of strain | Dry wt of cells (mg/ml) | Degree of urea degradation | | | Simultaneous liberation of $NH_3$ | +) |
|---|---|---|---|---|---|---|
| | | Total quantity degraded (mg/ml) | Speed of degradation ($\mu M$ of urea/mg dry wt of cells · min) | Degradation efficacy (%) | | |
| 44 | 3.6 | 33 | $5.48 \cdot 10^{-2}$ | 33 | ± | ++) |
| 47 | 3.2 | 34 | $5.94 \cdot 10^{-2}$ | 34 | + | +++) |
| 50 | 3.6 | 46 | $4.44 \cdot 10^{-2}$ | 46 | ± | |
| 577 | 3.6 | 57 | $9.56 \cdot 10^{-2}$ | 57 | + | |
| 578 | 3.5 | 61 | $12.53 \cdot 10^{-2}$ | 61 | + | |
| 579 | 3.7 | 60 | $9.96 \cdot 10^{-2}$ | 60 | + | |
| 677 | 1.9 | 75 | $30.57 \cdot 10^{-2}$ | 75 | + | |

+) Results of preliminary tests. Presence of $NH_3$ transient as it is utilized quickly by other microorganisms
++) ± presence of $NH_3$ uncertain (< 1 $\mu g/ml$)
+++) + $NH_3$ concentration low (~ 1 $\mu g/ml$)

Numerous soil bacteria strains biodegraded creatinine rapidly. 432 (59.3%) out of 729 soil bacteria strains utilized creatinine as the sole nitrogen source and 170 (23.4%) were able to utilize creatinine both as the nitrogen and carbon source. Table 3 shows the bacterial degradation of creatinine by three selected soil bacteria strains. Cell mass was incubated 30 minutes at +37° C.

Table 3

| No. of strain | Dry wt of cells (mg/ml) | Degree of creatinine degradation | | | Simultaneous liberation of $NH_3$ | +) |
|---|---|---|---|---|---|---|
| | | Total quantity degraded (mg/ml) | Speed of degradation ($\mu$M of creatinine/mg dry wt of cells · min) | Degradation efficacy (%) | | |
| 20 | 1.2 | 2.1 | $5.89 \cdot 10^{-4}$ | 21 | + | ++) |
| 591/a | 1.2 | 3.6 | $9.60 \cdot 10^{-4}$ | 36 | — | +++) |
| 591/b | 4.3 | 8.9 | $9.25 \cdot 10^{-4}$ | 89 | — | |
| 656 | 3.8 | 4.3 | $4.47 \cdot 10^{-4}$ | 43 | — | |

+) Results of preliminary tests. Presence of $NH_3$ transient as it is utilized quickly by other microorganisms
++) + $NH_3$ concentration low ($\sim \mu$g/ml)
+++) — $NH_3$ not present The biodegrading capacities for the NPN compounds are shown in table 1. The following observation was important in view of the object of the invention. In biodegradation and biosynthesis of protein, formation of ammonia needs particular consideration. Table 1 shows that liberation of ammonia as a result of bacterial degradation of proteins is not a necessary sequence. There were numerous soil bacteria strains which did not produce ammonia in measurable amounts. Accordingly 103 (72.1%) strains out of 153 tested strains biodegraded creatine, and 96 (58.1%) out of 165 tested strains biodegraded creatinine without liberation of ammonia. Although strains 591/b and 656 (table 3) within 30 minutes degraded 89% and 43% resp., creatinine, no ammonia formation was detectable. Either these soil bacteria did not liberate ammonia at all or there was a transient ammonia liberation which was utilized by the same bacteria. Important was the observation that there were also strains which utilized ammonia as the sole nitrogen source.

Conclusion: The result is that there are numerous soil microorganism strains which in vitro tests rapidly biodegrade significant amounts of just those NPN compounds which are known to accumulate in the body of uremic patients. Many strains have a very high biodegrading capacity and are able to degrade up to 90% of the NPN compounds used as the substrate. Of the tested 729 soil microorganisms, there were about 30 different bacteria strains which were able to degrade all of the 12 NPN compounds. The bacteria utilized these NPN compounds either as the sole nitrogen or simultaneously as nitrogen and carbon (energy)source.

EXPERIMENT 4

This test concerns normal and uremic dogs which were treated with soil bacteria. When normal dogs were administered orally lyophilized soil bacteria selected according to experiment 3, no blood abnormalities developed. Especially no increase in the blood-ammonia concentration appeared. Also there were no changes in the blood-urea and -creatinine concentrations.

Conclusion: When the same bacteria were administered to uremic dogs the general condition of the animals impoved, anorexia and insomnia disappeared and the body weight increased. Quantitative measurements showed that the ammonia value in the blood did not increase. In contrast thereto, the blood-urea and -creatinine concentration decreased to a significant degree.

Thus, the experiments with the dogs show firstly that the administration of lyophilized soil bacteria to normal and uremic animals did not cause any significant damages, secondly, that in uremic dogs the blood-urea and -creatinine values decreased, and thirdly, that the ammonia concentration did not increase.

EXPERIMENT 5

This experiment was carried out on 6 adult voluntary test persons and 4 uremic patients in which changes in the blood-ammonia, -urea and -creatinine values were investigated. For the treatment, five strains were selected from the 729 soil bacteria strains isolated by cultivation in accordance with experiment 3. Three of these strains were urea degrading, identified as Serratia spp., two of the bacteria strains degraded creatinine, and of these two, one was a non-fluorescent Pseudomonas spp., and the other was identified as belonging either to Rhizobium or Agrobacterium. The identification was carried out according to Breed et al. ("Bergey's Manual of Determinative Baceteriology", 7th edition, Williams and Wilkins, Baltimore, 1957) and according to Skermann, V.B.D. "A Guide to Identification of the Genera of Bacteria", 2nd edition, Williams and Wilkins, Baltimore, 1967). The five strains were non-hemolytic and sulphon amide sensitive and with an optimal growth temperature of +28° C. The pure cell mass was measured into a 1 molar glucose solution used as stabilizer (ratio 1:1) and freezed in liquid nitrogen, 72 hours in a lyophilization device at −50° C and a chamber pressure of 0.03 torr. The preparations were exposed to argon gas prior to contact with atmospheric oxygen, and packed into Snap-Fit capsules which had been made intestine soluble with Eudragit L 12.5 P. At every stage of preparation, testing of a possible bacterial contamination was carried out. Each gelatine capsule contained cells from only one of the selected pure soil bacteria strains at an average of 175 mg of each dried preparation. All test persons underwent the same treatment, receiving daily the same number of capsules containing on the one hand, a strain of a urea degrading soil bacteria and on the other hand, capsules containing a strain of creatinine degrading soil bacteria. Up to 15 + 15 capsules were administered per day and per person. Totally about 4500 capsules were administered, 175 to 400 per test person. Some of the test persons were administered up to 1000 capsules. The urea and creatinine concentrations in the blood were measured daily by known methods. Because of safety reasons only short treatment periods (10 to 14 days) were used in the experiments with the uremic patients. The total treatment period was 150 days.

Results: In the 6 voluntary test persons no unfavourable reactions, such as sickness, diarrhea, loss of weight, ammonia accumulation in blood or urea and creatinine changes, as a result of the intake of soil bacteria were observed. The 4 hospitalized uremic patients who were on a 40 g protein containing, but otherwise relatively free diet, suffered from severe anemia. Diarrhea did not appear. There was no accumulation of $NH_3$ in the blood. The soil bacteria treatment influenced both the creatinine and the urea concentration of the blood:

maximum decrease of creatinine 30%, of urea 49% in about 14 days. The decreases in both NPN values followed in a parallel fashion to each other. As to patient No. 1, the experiment was occasionally interrupted when the urea and creatinine values had decreased in a significant manner. Both values increased — as expected — again until the soil bacteria treatment was restarted. Subsequently the values decreased again as a result of the bacterial treatment. In all of the four uremics the blood values increased after the interruption of treatment. Thus for example patient No. 1 showed a blood creatinine value of 12.5 mg% (i.e. an increase of 100%) after a further eight weeks without treatment. In a further fifth patient on a domestic diet (11 years of essential hypertony, retinal abnormalities and papillanecrosis of the kidneys) the blood-creatinine value decreased from an initial value of 3.4 to 2.0 mg%, i.e. a decrease of 40%, and the urea concentration from 90 to 63 mg% within 14 days after administration of 280 capsules.

Conclusion: The blood-creatinine and -urea values may be influenced to a significant degree by means of conventional methods. The maximum decrease in the blood-creatinine value was 30 to 40%, that of the urea value almost 50% within 10 to 14 days.

Thus it is observed that versatile active, purposefully selected soil bacteria which are continuously administered into the human gut are able to biodegrade from significant to highly significant amounts of at least certain predetermined NPN compounds which, as known, accumulate in the body of kidney patients. It is also obvious that the "uremia toxines" are not so called end products which necessarily will have to be excreted. Clinical experiments show further that at least some of the uremic symptoms disappeared as a result of this treatment. Experiments 1 and 3 showed that some strains of soil bacteria were able to utilize very great amounts of different NPN compounds. Some strains were capable of biodegrading one single, specific NPN compound and some several NPN compounds. It thus follows, considering the possibilities of the modern microbiological techniques and their utility in the general technology, that non-pathogenic soil bacteria can be isolated and/or adapted specifically to NPN degradation purposes. As the NPN compounds in the body of kidney patients are formed in different metabolic ways and take part in these, it would be favourable to isolate a whole series of NPN utilizing soil bacteria and/or adapt them by means of specific induction methods. In this way, several metabolic cycles could be tackled simultaneously. On the other hand it is apparent that an administration of versatile soil microorganisms during the whole life of the kidney patient is perhaps not sufficient. Patients suffering from irreversible renal failure have to be kept on a suitable diet including high-degree proteins, such as, essential amino acids, energy releasing basic substances, such as, hydrocarbons, certain sugars, certain fatty acids, catalysts, vitamins. The water intake should correspondingly be limited. Commercial diets exist already for which relatively small amounts of water are required. Depending on the symptoms which might appear in the kidney patients, such as, e.g., arterial hypertony and/or different types of renal dependent anemia, antihypertonic and/or haematopoesis stimulating drugs may be administered together with the present basic components.

So far, the effects of soil bacteria on 12 different NPN compounds have been investigated either in vitro or in vivo on living objects. As all the tests have given possible results it may be presumed that also other NPN compounds may be biodegraded, in a similar manner.

The purpose of the basic component according to the invention is primarily to relieve uremic symptoms. It is however evident that also other NPN compounds forming in excess under different pathological circumstances, may also be biodegraded according to the invention. For example, the use of ornithine degrading soil bacteria might be valuable for the treatment of certain types of hypertonic conditions. Also certain illnesses which are characterized by an increased excretion of some amino acids, could be treated in a similar way.

The invention is illustrated in the following examples, whereby it is to be noted that the invention is not limited to these examples. It is to be noted that on the one hand almost an unlimited number of NPN compounds and their derivatives, and on the other hand an almost infinite number of soil bacteria strains exist. It thus follows that there is an unlimited number of possibilites and/or alternatives. The following examples are directed on only a few preparatory details, which when used in laboratory and for clinical experiments have led to versatile results.

EXAMPLE 1

This Example concerns the preparation of urea degrading basic components. Urea belongs to those NPN compounds which are most easily degraded by bacteria. It is not important the soil bacteria or the bacteria originate from a registered bacterial collection or have been obtained in connection with the specially cultured pure bacterial cultures. The most important characteristics are firstly the activity and the adaption capability of the enzyme system, and secondly, the non-pathogenity of the bacteria. Different strains of Serratia are especially well adapted for the degradation of urea, particularly the strains No. 577 to 579 of the collection. When the strain of the urea degrading bacteria has been selected, pure cultures may be prepared in order to control that only one type of cells grows in the culture medium. Although soil bacteria with constitutive enzyme systems exist (vide supra) which biodegrade urea, it is more favourable and safer to use bacteria with specifically adapted (induced) enzyme systems. The following composition for culturing was tested in practice and is recommended: thiamine, pyridoxine, Ca-pantothenic acid, nicotinic acid, p-amino benzoic acid, each in an amount of 0.25 mg, 0.5 mg of folic acid, 1 $\mu$g of $B_{12}$ vitamin and 0.5 $\mu$g of biotine, 1.0 g of $K_2HPO_4$, 1.5 g of $NaH_2PO_4 \cdot 4H_2O$, 0.05 g of $MnCl_2 \cdot 4H_2O$, 0.1 g of $MgSO_4 \cdot 7H_2O$, 0.01 g of $FeSO_4 \cdot 7H_2O$ and 1.0 g of yeast extract and 10 g/1000 ml urea pH 7.0 to 7.5. If urea acts as a nitrogen source, 5.0 g per 1000 ml of glucose is added. Glycerol is more advantageous than glucose while it stimulates the evolution and/or increases the activity of ureases. Also, other carbon sources may be employed. The bacterial mass is prepared at a temperature of +28° C using an incubation time of 1 to 3 days. For the production of the bacterial mass fermentators are used. A suitable aerating capacity is about 40 l/min. Because of practical reasons, it is preferred to use fermentators with an effective mixing capacity of 1000 l. When the growth rate corresponds to the desired one, the bacterial mass is washed at least four times in a conventional manner. The washing should take place in such a manner that the NPN compound (in this case urea as a substrate) is totally removed. The NPN compounds (=substrate) might if present create toxic symptoms. To the washed mass, a stabilizing agent, preferably a 1 molar glucose solution is added at a ratio of 1:1. The pure bacterial mass is preferably freezed in liquid nitrogen and kept at this low temperature until it is transferred into a lyophilizing device for a period of 48 to 72 hours. The chamber temperature is −50° C, and the chamber pressure 0.03 torr. resp. as low as is technically possible.

The freezedried bacterial mass is, prior to its contact with the unfavourable action of atmospheric oxygen, exposed to an inert gas, preferably argon. The freezedried bacterial mass is packed under aseptic conditions, e.g. in suitable capsules (by hand or in suitable automatic machines). Chemical, microscopic and bacteriologic tests are performed at every working stage in order to eliminate possible comtaminants. The capusles and/or other suitable shells are coated with known substances and/or methods. Thus commercial resins may be used whereby the type and/or the composition of the coating substances are so chosen that the final preparation (= the desired NPN compound degrading basic component) is liberated in a predetermined part of the intestine. The urea degrading activity of the freezedried soil bacteria must always be determined. The yield when employing a fermenting vessel with a capacity or volume of 1000 l, is 5 to 10 kgs of dry preparation. Also moist, i.e. initial bacterial masses may be used although the biodegrading capacity of the soil bacteria decrease rapidly in this state. The strains No. 47, 577 to 579 and 677 of the collection are the most active.

EXAMPLE 2

This Example concerns the preparation of creatinine degrading basic substance. The general technical characteristics are the same as in Example 1. In some cases, the creatine degrading soil microorganisms are also capable of degrading creatinine. The basic growth medium may contain a smaller amount of yeast extract than in the adaptation of the urea degrading microorganisms, as the creatinine molecule contains more carbon than the urea molecule. Some of the experiments showed that of the creatinine degrading soil bacteria, three species had an especially high activity: two of them are nonfluorescent Pseudomonas, one is either Rhizobium or Agrobacterium (strains No. 691, 601 and 565) of the collection. The following microorganisms are also capable of degrading creatine/creatinine: Corynecaterium ureafaciens, i.e. *Arthrobacter ureafaciens, Escherichia coli, Pseudomonas aeruginosa*.

EXAMPLE 3

This Example concerns the preparation of uric acid degrading basic components. The general technical characteristics are the same as in Example 1. Uric acid is used as a substrate in which the corresponding microorganisms are adapted. Strains No. 93, 222, 260, 265, 281, 366, 373, 376, 415, 525, 557 of the collection are active and capable of degrading uric acid: *Bacillus subtilis, Bacillus fastidosus, Micrococcus dentrificans, Myobacterium phlei, Aerobacter aerogenes, Fusarium moniliforme, Histoplasma capsulata, Penicillinum chrysogenum*.

What we claim is:

1. Method for alleviating uremic symptoms in persons suffering from renal failure comprising administering orally thereto an effective dosage of a cell mass of a non-pathogenic soil bacteria selected from the group consisting of an urea degrading bacteria, a creatine degrading bacteria, a creatinine degrading bacteria and an uric acid degrading bacteria.

2. Method according to claim 1 wherein the urea degrading soil bacteria is a Serratia species.

3. Method according to claim 1 wherein the creatinine degrading bacteria is Pseudomonas, species.

4. Method according to claim 1 wherein the cell mass is lyophilized.

5. The method according to claim 1 wherein the creatinine degrading bacteria is Rhizobium species.

6. The method according to claim 1 wherein the creatinine degrading bacteria is Agrobacterium species.

* * * * *